United States Patent
Bauer et al.

(10) Patent No.: US 9,926,341 B2
(45) Date of Patent: Mar. 27, 2018

(54) COPOLYMERS FOR PROTEIN PRECIPITATION

(71) Applicant: Merck Patent GmbH, Darmstadt (DE)

(72) Inventors: Johann Bauer, Darmstadt (DE); Almut Rapp, Darmstadt (DE); Bernd Stanislawski, Frankfurt am Main (DE); Florian Capito, Darmstadt (DE)

(73) Assignee: Merck Patent GmbH, Darmstadt (DE)

(*) Notice: Subject to any disclaimer, the term of this patent is extended or adjusted under 35 U.S.C. 154(b) by 194 days.

(21) Appl. No.: 14/652,517

(22) PCT Filed: Nov. 25, 2013

(86) PCT No.: PCT/EP2013/003552
§ 371 (c)(1),
(2) Date: Jun. 16, 2015

(87) PCT Pub. No.: WO2014/094957
PCT Pub. Date: Jun. 26, 2014

(65) Prior Publication Data
US 2015/0329589 A1   Nov. 19, 2015

(30) Foreign Application Priority Data

Dec. 20, 2012 (EP) .................................... 12008475

(51) Int. Cl.
*C07K 1/32* (2006.01)
*C07K 1/30* (2006.01)
*C07K 16/00* (2006.01)

(52) U.S. Cl.
CPC ................. *C07K 1/30* (2013.01); *C07K 1/32* (2013.01); *C07K 16/00* (2013.01); *C07K 2317/10* (2013.01)

(58) Field of Classification Search
None
See application file for complete search history.

(56) References Cited

U.S. PATENT DOCUMENTS

| | | | |
|---|---|---|---|
| 5,455,147 A * | 10/1995 | Chen | G03C 7/3275 430/449 |
| 5,922,531 A | 7/1999 | Dubin et al. | |
| 6,307,013 B1 | 10/2001 | Chivers | |
| 6,927,282 B2 | 8/2005 | Chivers et al. | |
| 7,795,041 B2 | 9/2010 | Hatton et al. | |
| 7,947,813 B2 | 5/2011 | Fahrner et al. | |
| 8,163,886 B2 | 4/2012 | Moya | |
| 8,362,217 B2 | 1/2013 | Moya et al. | |
| 8,691,918 B2 | 4/2014 | Jaber et al. | |
| 9,217,048 B2 | 12/2015 | Jaber et al. | |
| 9,731,288 B2 | 8/2017 | Jaber et al. | |
| 2002/0058786 A1 | 5/2002 | Chivers | |
| 2005/0215687 A1 | 9/2005 | Hatton et al. | |
| 2008/0193981 A1 | 8/2008 | Fahrner et al. | |
| 2008/0255027 A1 | 10/2008 | Moya et al. | |
| 2009/0036651 A1 | 2/2009 | Moya | |
| 2010/0267933 A1 | 10/2010 | Wilson | |
| 2011/0313066 A1 | 12/2011 | Jaber et al. | |
| 2013/0123476 A1 | 5/2013 | Moya | |
| 2013/0137860 A1 | 5/2013 | Moya et al. | |
| 2014/0171594 A1 | 6/2014 | Jaber et al. | |
| 2016/0067703 A1 | 3/2016 | Jaber et al. | |

FOREIGN PATENT DOCUMENTS

| | | |
|---|---|---|
| JP | 2007-528784 A | 10/2007 |
| JP | 2010-516773 A | 5/2010 |
| WO | 2008079280 A1 | 7/2008 |
| WO | 2008091740 A2 | 7/2008 |
| WO | 2011/146394 A1 | 11/2011 |

OTHER PUBLICATIONS

Hirsch, Frederic et al, "The electrical conductivity of blood." Blood (1950) 5 p. 1017-1035.*
The GenBank entry AAA51411 for BSA, entered Feb. 11, 2002.*
The Invitrogen literature describing Dynabeads® in immunoprecipitation, 2008, publication O-076281-rl US 0308.*
GenBank entry AJR02271 for protein G, submitted Jan. 2013.*
International Search Report from PCT Application No. PCT/EP2013/003552 dated Mar. 6, 2014.
Adith Venkiteshwaran et al. "Selective Precipitation-Assisted Recovery of Immunoglobulins From Bovine Serum Using Controlled-Fouling Crossflow Membraine Microfiltration" Biotechnology and Bioengineering, (2008), vol. 101, No. 5, pp. 957-966.
Jue (Michelle) Wang, et al. "Precipitation of Process-Derived Impurities in Non-Protein A Purification Schemes for Antibodies" BioPharm International, Contract Manufacturing, (2009), 11 pages.
Massimo Temponi et al. "Purification of Murine IgG Monoclonal Antibodies by Precipitation with Caprylic Acid: Comparison with Other Methods of Purification" Hybridoma, (1989), vol. 8, No. 1, pp. 85-95.
Chandra Mohan "Buffers—A guide for the preparation and use of buffers in biological systems" Calbiochem, (2003) (37 pages).
Japanese Office Action dated Aug. 24, 2017 issued in corresponding JP 2015-548253 application (5 pages).
English Abstract of WO 2005/076938 A2 corresponding to JP 2007-528784 A published Oct. 18, 2007.
English Abstract of WO WO 2008-091740 A2 corresponding to JP 2010-516773 A published May 20, 2010.

* cited by examiner

*Primary Examiner* — Fred H Reynolds
(74) *Attorney, Agent, or Firm* — Millen White Zelano & Branigan, P.C.

(57) ABSTRACT

The present invention relates to the isolation of recombinant and/or biotherapeutic proteins for capture or clarification from cell culture fluid using copolymers. The copolymers used according to the process of the present invention comprise hydrophobic and anionic residues.

16 Claims, 3 Drawing Sheets

AMPS- ABZ copolymer          AMPS- BzAAm copolymer

Fig. 3a
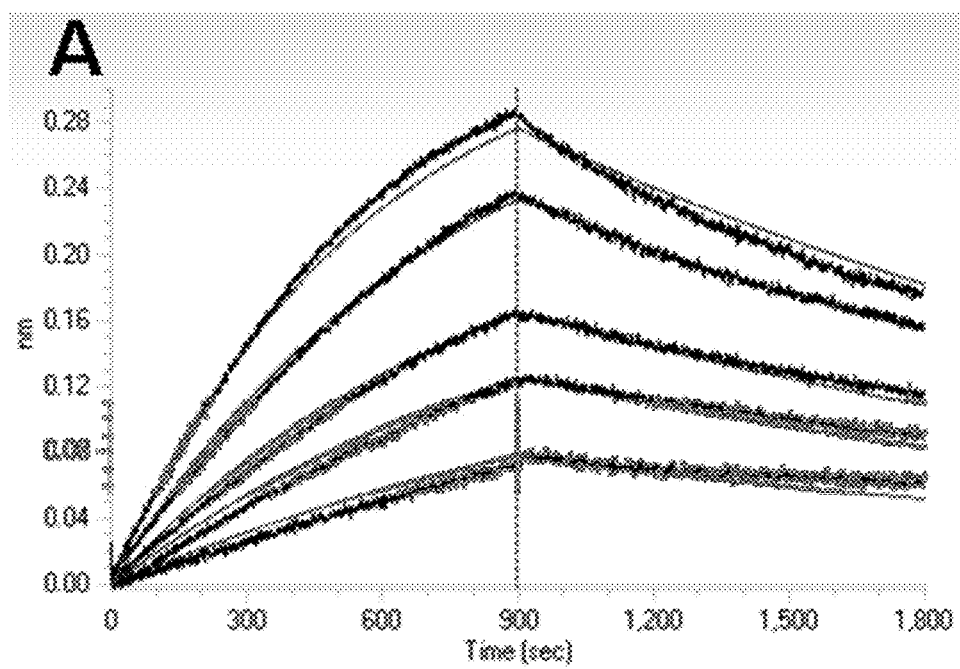
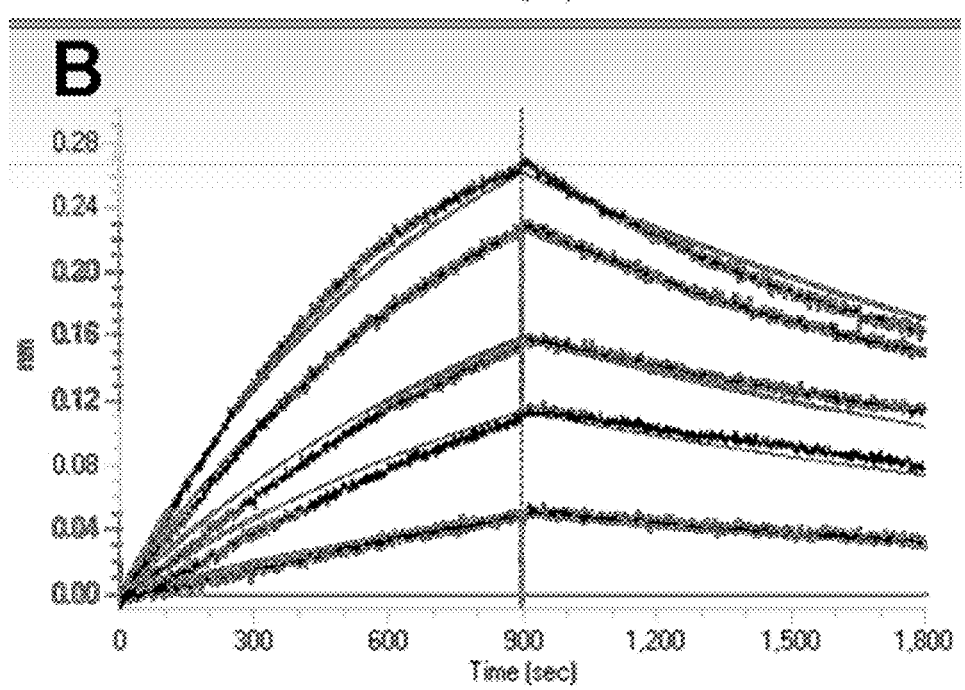
Fig. 3b

COPOLYMERS FOR PROTEIN PRECIPITATION

The present invention relates to the purification of target molecules like recombinant and/or biotherapeutic proteins for capture or clarification from cell culture fluid using copolymers. The copolymers used according to the process of the present invention comprise hydrophobic and anionic residues.

BACKGROUND OF THE INVENTION

Monoclonal antibodies (mAbs) are widely used in clinical application, diagnostic systems and different research field. Production of these proteins using mammalian cell expression systems has grown tremendously since the production of the first licensed mAb in 1986. To-date, mainly three different cell lines are used for mAb production: chinese hamster ovary (CHO), murine myeloma (NS0) and Sp2/0 cells, while production takes place in bioreactors ranging from 5000 to 25000 liters. Downstream processing of antibodies and biotherapeutic proteins in general uses a series of purification steps, starting with harvesting of the fermenter, e.g. using disk stack centrifuges, followed by clarification through depth- and membrane filter systems. Afterwards, several chromatography steps are used, starting with initial capture using affinity chromatography with Protein A, followed by anion- and cation exchange chromatography. Additional chromatography steps can involve hydrophobic or hydrophilic interaction chromatography and size exclusion chromatography. Virus inactivation is achieved via low pH elution and additional filtration remove residual virus particles. However, increasing cell culture expression levels of 10-13 g $l^{-1}$ nowadays compared to 1 g $l^{-1}$ 25 years ago, as well as rising economic pressure, require the need for enhanced purification methods with higher yield and throughput compared to the performance of current chromatography-based systems. These demands may be met by either increasing chromatography column material capacity, dimensions of columns or developing alternative means of purification to chromatography, which should obtain comparable yields and purities, however, decrease costs and be better scalable. For large scale areas, batch purification methods have been developed, where the desired protein is precipitated out of the harvest cell solution. Common methods for protein precipitation are hereby ammonium sulphate precipitation (AS) (Venkiteshwaran, Heider, et al., 2008), polyethylene glycol (PEG) precipitation, or using caprylic acid as precipitant (Wang, Diehl, et. al., 2009; Temponi, Kageshita, et al., 1989). However, using PEG or AS for large-scale purification requires large amounts of these precipitants and higher protein concentrations, yielding only moderate purity grades, producing a high waste load. The existing purification methods are expensive, very laborious with large buffer volumes and low throughput (chromatography) or lack sufficient purity and yield (precipitation). The elution of bound mAb from protein A at low pH can form immunogenic aggregates, removing them and leaching protein A increases costs further. Thus, alternative means to protein A chromatography and improvements in protein and antibody purification are urgently required. Additionally, fragment antigen binding regions of antibodies are gaining increasing interest for applications in diagnostics and therapy. To obtain such fragments, endopeptidases can be used.

Treatment of a monoclonal antibody with papain is a common way to produce antigen binding fragments or fragment antigen binding, also resulting in production of a Fc fragment, representing the constant region of an antibody. Fab and Fc can be separated using protein A affinity chromatography, however, this separation technique is insufficient for Fabs derived from mAbs belonging to the $V_H3$ subfamily, due to a binding affinity of protein A to this type of Fab. Humanized mAbs largely rely on gene sequences with $V_H3$ abundance. Additionally; human phage display libraries exhibit a large presence of $V_H3$'s. Therefore, alternative strategies for separating Fab and Fc fragments are required. Modified protein A is one option, however rather cost-intensive.

A very recent approach pursued is the use of polymers as precipitants which might be applied to a greater number of antibodies without the demand for customizing.

U.S. Pat. No. 6,927,282 discloses the use of anionic polymers with different charge densities for polymer flocculation. U.S. Pat. No. 5,922,531 deals with the use of controlled pore glass treated with polyelectrolyte layers for protein adsorption. WO 2008/079280 discloses the use of polyelectrolytes that are soluble under certain conditions and precipitate out of solution upon a change in the conditions.

WO 2008/091740 discloses the use of polyanionic or polycationic polymers for protein precipitation.

This shows that the approach of using polymers as precipitants gains more and more interest. Yet there is still the problem to find a method that is efficient enough to be suitable for biopharma production. In addition, there is still the problem to adjust and optimize the procedure for different target molecules.

BRIEF DESCRIPTION OF THE INVENTION

It has been found that polymers with anionic and hydrophobic properties—so called anionic mixed mode polymers—are ideal polymers for protein precipitation. By using a polymer that comprises hydrophobic and anionic groups, antibodies can be precipitated from clarified cell culture media in yields of up to 90% and more antibody recovery in good purities.

The present invention is therefore directed to a method for separating or isolating a target molecule from a sample comprising:
a) Providing the sample
b) Adding one or more copolymers comprising hydrophobic and anionic groups to the sample whereby a target molecule-copolymer precipitate is formed
c) Separating the precipitate from the mixture of step b)

In a preferred embodiment, the copolymer comprises 35 to 65% anionic groups.

In one preferred embodiment, the anionic groups comprise sulfonic acid, sulphuric acid, carboxylic acid and/or phosphonic or phosporic acid.

In another preferred embodiment, the hydrophobic groups comprise linear, branched or cyclic alkyl groups, halogen substituted alkyl groups, aromatic groups, heteroaromatic groups and/or halogen substituted aromatic or heteroaromatic groups.

In another preferred embodiment, the copolymer has a weight average molecular weight between 10.000 and 120.000 g/mol and/or polydispersities between 1.05-2.50.

In a preferred embodiment, the target molecule is an antibody.

In another preferred embodiment the target molecule is either the Fc (fragment constant region) part or the Fab (fragment antigen binding) region of an antibody.

In a preferred embodiment, in step a) the pH of the sample is adjusted to a pH below the isoelectric point of the target molecule and, if applicable, above the isoelectric point of other components of the sample from which it shall be separated.

In a preferred embodiment, in step a) the pH of the sample is adjusted to a pH between 4 and 5.5.

In another preferred embodiment, the ionic strength of the sample is adjusted to be similar to a conductivity of 17 mS/cm or less, measured at 20° C.

In another preferred embodiment, in a further step d), the precipitate from step c) is re-dissolved.

In another preferred embodiment, the re-dissolved mixture of step d) is treated with silica or glass flakes.

In another preferred embodiment, the silica or glass flakes are functionalized with DMAE and/or TMAE groups.

BRIEF DESCRIPTION OF THE DRAWINGS

FIG. 3 shows a sensorgram after Biolayer interferometry (BLI) of
a) a non-precipitated monoclonal antibody
b) a precipitated and redissolved monoclonal antibody, treated with the enclosed purification technique,
which reveal no difference in the binding affinity of precipitated and non-precipitated antibody. Red lines represent a global fit of the data to a 1:1 interaction model. Data collected using Octet Red. Kinetics of non-precipitated and precipitated antibody measured in the same antigen containing wells (6, 4, 3, 2 and 1 nM).

DEFINITIONS

Figure 1:
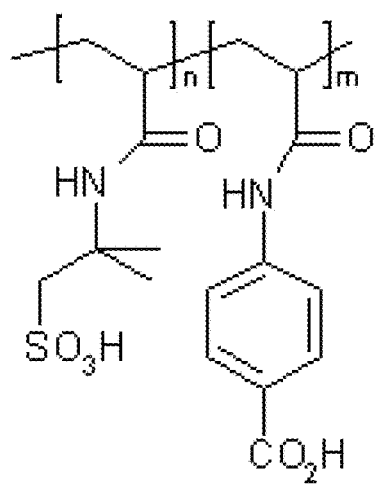
FIG. 1 shows the chemical structures of different types of suitable building blocks for the copolymers to be used in the method of the invention.
Figure 1:
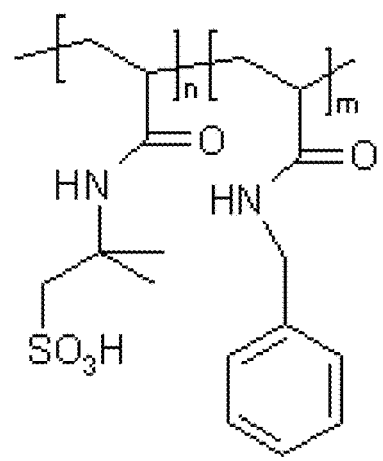

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a ligand" includes a plurality of ligands and reference to "an antibody" includes a plurality of antibodies and the like.

Unless defined otherwise, all technical and scientific terms used herein have the same meaning as commonly understood by one of ordinary skill in the art to which this invention is related. The following terms are defined for purposes of the invention as described herein.

As used herein the term "target molecule" refers to any molecule, substance or compound that shall be isolated, separated or purified from one or more other components, e.g. impurities, in a sample. Examples of target molecules are antibodies, fragment antigen binding (Fab), fragment constant region (Fc), proteins, peptides, recombinant proteins, other natural compounds, other biopharmaceutical compounds, vaccines or aggregates of biopharmaceutical compounds. In a preferred embodiment, the target molecule is a biomolecule, preferably a protein. In a very preferred embodiment, the target molecule is an antibody. Typically the target molecule is the product that shall be isolated by applying the method of the present invention but it is also possible to use the method of the invention to precipitate a target molecule that is not the product to be isolated. In this case the target molecule is a component that shall be removed while the final product remains in the supernatant and is purified by removing the target molecule. When using the present invention for purification and separation of Fab and Fc fragments, it is for example possible that the target molecule that is precipitated is the wanted product but it is also possible to precipitate one type of fragments while the wanted product is the fragment remaining in the supernatant. In any case the component that is precipitated is called the target molecule.

The term "antibody" refers to a protein which has the ability to specifically bind to an antigen. Typically, antibodies are having a basic four-polypeptide chain structure consisting of two heavy and two light chains, said chains being stabilized, for example, by interchain disulfide bonds. Antibodies may be monoclonal or polyclonal and may exist in monomeric or polymeric form, for example, IgM antibodies which exist in pentameric form and/or IgA antibodies which exist in monomeric, dimeric or multimeric form. Antibodies may also include multispecific antibodies (e.g., bispecific antibodies), and antibody fragments so long as they retain, or are modified to comprise, a ligand-specific binding domain. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. When produced recombinantly, fragments may be expressed alone or as part of a larger protein called a fusion protein.

Exemplary fragments include Fab, Fab', F(ab')2, Fc and/or Fv fragments.

Exemplary fusion proteins include Fc fusion proteins. According to the present invention fusion proteins are also encompassed by the term "antibody".

As discussed above, in some embodiments, an antibody is an Fc region containing protein, e.g., an immunoglobulin. In some embodiments, an Fc region containing protein is a recombinant protein which includes the Fc region of an immunoglobulin fused to another polypeptide or a fragment thereof. Exemplary polypeptides include, e.g., renin; a growth hormone, including human growth hormone and bovine growth hormone; growth hormone releasing factor; parathyroid hormone; thyroid stimulating hormone; lipoproteins; $\alpha$-1-antitrypsin; insulin $\alpha$-chain; insulin $\beta$-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-$\alpha$ and -$\beta$; enkephalinase; RANTES (regulated on activation normally T-cell expressed and secreted); human macrophage inflammatory protein (MIP-1-$\alpha$); a serum albumin such as human serum albumin; Muellerian-inhibiting substance; relaxin $\alpha$-chain; relaxin $\beta$-chain; prorelaxin; mouse gonadotropin-associated peptide; a microbial protein, such as $\beta$-lactamase; DNase; IgE; a cytotoxic T-lymphocyte associated antigen (CTLA) (e.g., CTLA-4); inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as αFGF and βFGF; epidermal growth factor (EGF); transforming growth factor (TGF) such as TGF-alpha and TGF-β, including TGF-β1, TGF-β2, TGF-β3, TGF-β4, or TGF-β5; insulin-like growth factor-I and -II (IGF-I and IGF-II); des(I-3)-IGF-I (brain IGF-I), insulin-like growth factor binding proteins (IGFBPs); CD proteins such as CD3, CD4, CD8, CD 19 CD20, CD34, and CD40; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (Ls), e.g., IL-I to IL-IO; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CDI Ia, CDI Ib, CDI Ic, CD 18, an ICAM, VLA-4 and VCAM; a tumor associated antigen such as HER2, HER3 or HER4 receptor; and fragments and/or variants of any of the above-listed polypeptides. In addition, an antibody according to the present invention is any protein or polypeptide, fragment or variant thereof, that binds specifically to any of the above-listed polypeptides.

As used herein, and unless stated otherwise, the term "sample" refers to any composition or mixture that contains a target molecule. Samples may be derived from biological or other sources. Biological sources include eukaryotic and prokaryotic sources, such as plant and animal cells, tissues and organs. Preferred samples are from cell culture fluid like mammalian cell culture, e.g. CHO, NS-0, SP2/0, BioWa, bacterial cell culture, e.g. *E. coli, B. subtilis*, yeast cell culture, or filamentous fungi. The sample may also include diluents, buffers, detergents, and contaminating species, debris and the like that are found mixed with the target molecule. The sample may be "partially purified" (i.e., having been subjected to one or more purification steps, such as filtration steps) or may be obtained directly from a host cell or organism producing the target molecule (e.g., the sample may comprise harvested cell culture fluid).

The term "impurity" or "contaminant" as used herein, refers to any foreign or objectionable molecule, including a biological macromolecule such as DNA, RNA, one or more host cell proteins, nucleic acids, endotoxins, lipids, impurities of synthetic origin and one or more additives which may be present in a sample containing the target molecule that is being separated from one or more of the foreign or objectionable molecules using a process of the present invention. Additionally, such impurity may include any reagent which is used in a step which may occur prior to the method of the invention.

The terms "purifying," "separating," or "isolating," as used interchangeably herein, refer to increasing the degree of purity of a target molecule by separating it from a composition or sample comprising the target molecule and one or more other components, e.g. impurities. Typically, the degree of purity of the target molecule is increased by removing (completely or partially) at least one impurity from the composition.

The term "chromatography" refers to any kind of technique which separates an analyte of interest (e.g. a target molecule) from other molecules present in a mixture. Usually, the target molecule is separated from other molecules as a result of differences in rates at which the individual molecules of the mixture migrate through a stationary medium under the influence of a moving phase, or in bind and elute processes.

The term "affinity chromatography" refers to a protein separation technique in which a target molecule (e.g., an Fc region containing protein of interest or antibody) is specifically bound to a ligand which is specific for the target molecule. Such a ligand is generally referred to as a biospecific ligand. In some embodiments, the biospecific ligand (e.g., Protein A or a functional variant thereof) is covalently attached to a chromatography matrix material and is accessible to the target molecule in solution as the solution contacts the chromatography matrix. The target molecule generally retains its specific binding affinity for the biospecific ligand during the chromatographic steps, while other solutes and/or proteins in the mixture do not bind appreciably or specifically to the ligand. Binding of the target molecule to the immobilized ligand allows contaminating proteins or protein impurities to be passed through the chromatography matrix while the target molecule remains specifically bound to the immobilized ligand on the solid phase material. The specifically bound target molecule is then removed in active form from the immobilized ligand under suitable conditions (e.g., low pH, high pH, high salt, competing ligand etc.), and passed through the chromatographic column with the elution buffer, free of the contaminating proteins or protein impurities that were earlier allowed to pass through the column. Any component can be used as a ligand for purifying its respective specific binding protein, e.g. antibody. However, in various methods according to the present invention, Protein A is used as a ligand for an Fc region containing target molecule. The conditions for elution from the biospecific ligand (e.g., Protein A) of the target molecule (e.g., an Fc region containing protein) can be readily determined by one of ordinary skill in the art. In some embodiments, Protein G or Protein L or a functional variant thereof may be used as a biospecific ligand. In some embodiments, a biospecific ligand such as Protein A is used at a pH range of 5-9 for binding to an Fc region containing protein, washing or re-equilibrating the biospecific ligand/target molecule conjugate, followed by elution with a buffer having pH about or below 4 which contains at least one salt.

The term "binding" as used herein to describe interactions between a target molecule (e.g., an Fc region containing protein) and a copolymer molecule refers to the generally reversible binding of the target molecule to a copolymer molecule through the combined effects of spatial complementarity of e.g. protein and copolymer structures at a binding site coupled with electrostatic forces, hydrogen bonding, hydrophobic interactions, and/or van der Waals forces at the binding site. Generally, the greater the spatial complementarity and the stronger the other forces at the binding site, the greater will be the binding specificity of a protein for its respective ligand. Non-limiting examples of specific binding includes antibody-antigen binding, enzyme-substrate binding, enzyme-cofactor binding, metal ion chelation, DNA binding protein-DNA binding, regulatory protein-protein interactions, and the like. Ideally, in affinity chromatography specific binding occurs with an affinity of about $10^{-4}$ to $10^{-8}$ M in free solution.

A "buffer" is a solution that resists changes in pH by the action of its acid-base conjugate components. Various buffers which can be employed depending, for example, on the desired pH of the buffer are described in Buffers. A Guide for the Preparation and Use of Buffers in Biological Systems, Gueffroy, D., ed. Calbiochem Corporation (1975). Non-limiting examples of buffers include MES, MOPS, MOPSO, Tris, HEPES, phosphate, acetate, citrate, succinate, and ammonium buffers, as well as combinations of these.

According to the present invention the term "buffer" is used for any liquid composition that is used a) to adjust the pH and/or ionic strength or other chemical or physical attributes of the solution containing the target molecule or any other molecule used within the scope of this invention, b) to wash the precipitated target molecule or any other molecule used within the scope of this invention, c) to redissolve the precipitated target molecule or any other molecule used within the scope of this invention According to the present invention, the terms "polymerization" or "synthesis of copolymers" can be used interchangeable and may refer to copolymer or polymer synthesis using one of the following techniques, but not limited to: free radical polymerization, living radical polymerization (ATRP, RAFT, NMP etc.), anionic or cationic polymerization, condensation polymerization or any kind of ring-opening polymerization. The free radical polymerization may be initiated e.g. thermally, photochemically, through redox reaction or electrochemically.

According to the present invention, monomer ratio is the molar ratio of one monomer type present in the copolymer to all other types of monomers present in the copolymer.

According to the present invention, the molecular weight of a copolymer is given in terms of weight average molecular weight (abbreviated as Mw when speaking about copolymers in the present invention), as determined by gel permeation chromatography, a standard method to determine the molecular weight of a copolymer, thus known to a person skilled in the art.

According to the present invention, the term polydispersity is the ratio of weight average molecular weight and number average molecular weight of a given copolymer.

"aliphatic" or "aliphatic group" means an optionally substituted, non-aromatic hydrocarbon moiety. The moiety may be, for example, linear, branched, or cyclic {e.g., mono- or polycyclic such as fused, bridging, or spiro-fused polycyclic}, or a combination thereof. Unless otherwise specified, aliphatic groups contain 1-30 carbon atoms, preferably 1 to 20, carbon atoms. Preferred aliphatic groups are alkyl groups.

"Alkyl groups" described herein are preferably lower alkyl containing from one to 20 carbon atoms, preferably 1 to 8 carbon atoms, in the principal chain and up to 30 carbon atoms altogether. They may be linear, branched or cyclic and include methyl, ethyl, propyl, butyl, pentyl, hexyl and the like.

The term "aromatic group" refers to optionally substituted monocyclic, bicyclic, and tricyclic ring systems having a total of five to fourteen ring members, wherein at least one ring in the system is aromatic and wherein each ring in the system contains three to seven ring members. Preferred are monocyclic or bicyclic groups containing from 6 to 12 carbons in the ring portion, such as phenyl, biphenyl, naphthyl, substituted phenyl, substituted biphenyl or substituted naphthyl.

A "hydrophobic group" is a moiety such as a substituent or residue which, when covalently attached to a molecule, such as a monomer or a polymer, instead of a hydrogen atom increases the molecule's hydrophobicity.

Detailed Description of the Invention
Synthesis/properties of Copolymer

According to the present invention, a copolymer is a polymer consisting of at least two different types of monomers. Preferably, the copolymer is linear and it is soluble in water and aqueous buffers, preferably at physiological salt conditions, comprising e.g. a conductivity of 10-20 mS/cm, measured at 20° C. The copolymer to be used in the method of the present invention comprises at least one type of anionic group and at least one type of hydrophobic group. In one embodiment, it contains only anionic and hydrophobic groups. According to the present invention, the term "anionic group" refers to negatively charged groups present in the copolymer. It is obvious to a person skilled in the art that the charge of the anionic group may only be present at certain pH conditions but in the non-charged state the anionic groups are capable of becoming anionic charged, e.g., upon removal of an electrophile (e.g., a proton (H(+)), for example in a pH dependent manner). The anionic group may be capable of electrostatic interactions and may be a strong ion exchanger, weak ion exchanger and/or capable of complexing metal ions. Anionic groups may be one of the following functional groups, but are not limited to: sulphonic acids and their salts —$SO_3$—, sulfuric acid esters/amides and their salts —$SO_4$—, —$NHSO_3^-$, phosphonic acid —$PO_3^{2-}$, phosphoric acid esters and their salts —$PO_4^{2-}$, carboxylic acids and their salts —$COO^-$. An example of a monomer unit suitable for introducing an anionic group in the copolymer is 2-Acrylamido-2-methyl-propane sulfonic acid (AMPS), vinyl sulfonic acid VS, styrene sulfonic acid or (meth)acrylic acid.

The hydrophobic group may be a linear, branched or cyclic aliphatic group, a halogen substituted alphatic group, an aromatic, heteroaromatic or halogen substituted aromatic group. An example of a monomer unit suitable for introducing a hydrophobic group in the copolymer is Benzylacrylamide (BzAAm) or Benzylmethacrylate (BzMA), N-isopropylacrylamide (NIPAM), Methylmethacrylate (MMA), Butylacrylate or tert-Butylacrylate.

In a preferred embodiment, the hydrophobic groups are further functionalized with an anionic group like sulfonic acid, carboxylic acid or phosphonic acid. An example of such a functionalized hydrophobic group is benzoic acid. An example of a monomer unit suitable for introducing a functionalized hydrophobic group in the copolymer is 4-(Acrylamido)benzoic acid 4-ABZ).

The copolymer according to the present invention typically comprises a copolymer backbone to which the anionic and hydrophobic groups are attached. Typically the copolymer is synthesized by polymerizing monomer units. The copolymer backbone may be any polymer that can be made via any type of polymerization like radical polymerization (e.g. free radical polymerization, living radical polymerization (ATRP, RAFT, NMP etc.), anionic or cationic polymerization, condensation polymerization or any kind of ring-opening polymerization. The free radical polymerization may be initiated e.g. thermally, photochemically, through redox reaction or electrochemically. Typical polymer backbones may be, but are not limited to: vinyl polymers (e.g. polyacrylates, polymethacrylates, polyacrylamide, polymethacrylamide, polystyrenes, polyvinylpyridines, polyvinylpyrrolidone), polyethers (e.g. polyethyleneglycol or polyethyleneoxide), polyesters, polyamides.

In Formula I to IV schematic representations of possible copolymers are given. The copolymer may be random or a block copolymer, preferably random. The following definitions apply:

R=polymer backbone
R'=spacer, which may or may not be present in the polymer
F=functional group (F1=anionic group, F2=hydrophobic group, F3 and F4=independent of each other any functional group or —H,
n>0, m>0, l≥0, k≥0

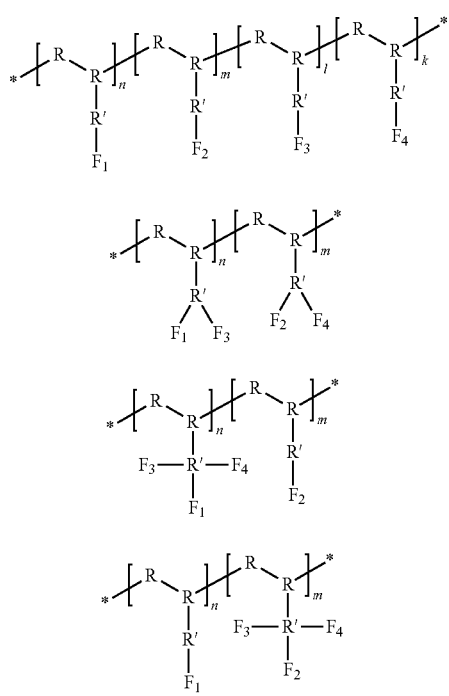

In Table 1 suitable examples of the polymer backbone (R) and the side groups of the polymer are defined, whereby a so-called side group consists of a functional group (F) and a spacer (R') or a functional group (F) alone if no spacer (R') is present.

In a preferred embodiment, each monomer unit that is used for synthesizing the copolymer has at least one hydrophobic or one anionic group.

TABLE 1 building blocks for polymers.

| polymer backbone (R) | vinyl polymers, polyethers, polyesters, polyamides | examples: polymethylmethacrylate, polymethacrylate, poly(vinyl acetate), polyacrylamide, poly(acrylic acid), polyacrylonitrile, polystyrene, poly(methylstyrene), polyvinylpyridine, polyvinylpyrrolidone, polyethylene, polybutadiene, polyisoprene, polyethylene oxide, polyethylene glycol, poly(ethyleneterephthalate, polycaprolactam, poly(phenylene terephthalamide), etc. |
|---|---|---|
| spacer (R') | alkyl (linear, branched, cyclic) halogen substituted alkyl (linear, branched, cyclic) aromatic heteroaromatic halogen substituted aromatic or heteroaromatic ester | |

TABLE 1-continued building blocks for polymers.

| | ether amide | |
|---|---|---|
| functional group (F) | anionic group group capable of pi-pi- interactions group capable of electrostatic interactions hydrophobic group | Examples: |

Very good results can be obtained with copolymers made at least of AMPS and 4-ABZ as well as AMPS and BzAAm.

Copolymers useful for the method of the invention typically have a weight average molecular weight ranging from about a thousand (1000) g/mol to about 1,100,000 g/mol and/or polydispersities polydispersities between 1.05-2.5. The copolymers of the invention may be used as a mixture of copolymers comprising the same type of monomeric units but with a broad range of chain lengths, i.e. a range of weight average molecular weight from about 1000 g/mol to about a million (1,000,000) g/mol, preferably with polydispersities between 1.05-2.5. The mixture may also have a narrow range of weight average molecular weight, for example from about 35.000 to about 45.000 g/mol, or from about 50.000 g/mol to about 55.000 g/mol, preferably all with polydispersities between 1.05-2.5. The weight average molecular weight and the profile of the molecular weight distribution may be controlled under certain polymerization conditions of the monomeric units such as concentration, polymerization initiator or catalyst, temperature, or time. The weight average molecular weight of the copolymers preferably is between 10.000 and 120.000 g/mol, most preferred between 35.000 and 60.000 g/mol, preferably with polydispersities between 1.05-2.5.

Out of the total number of anionic and hydrophobic groups, typically 10 to 90% of the groups are anionic groups.

Preferably 35 to 65%, most preferred 45 to 60% of the total number of anionic and hydrophobic groups are anionic groups.

The copolymers can be synthesized to specifically meet the requirements for selectively precipitating various target molecules, e.g. by employing copolymers of defined molecular weight, chain length or defined degree of hydrophobicity and composition.

Precipitation Process

The method of the present invention is directed to the purification of a target molecule that is typically present in a biopharmaceutical sample using copolymers comprising anionic and hydrophobic groups. When adding the copolymers to the sample solution, the copolymers bind to the target molecules and precipitate. To get optimal precipitation results the sample is provided and adjusted to certain conditions like target molecule concentration, pH and ionic strength. This can be done prior to the addition of the copolymer or in parallel. It has been found that using the copolymers according to the method of the present invention, one can achieve good precipitation results even if the sample has a high ionic strength up to a conductivity of 22.5 mS/cm, measured at 20° C. Typically, the ionic strength of the sample should be adjusted using appropriate dilution methods to a conductivity of 0 mS/cm to 22.5 mS/cm, preferably to a conductivity of 0 mS/cm to 17 mS/cm, with conductivity determined at 20° C. In contrast to many known procedures the method of the present invention allows for effective precipitation of the target molecule even at ionic strength between conductivities of 10 mS/cm to 22.5 mS/cm, determined at 20° C. The ionic strength may be modified or reduced by using appropriate dilution techniques or buffer exchange techniques.

In specific cases, notably separation of Fab from the Fc region after enzymatic treatment of a monoclonal antibody, adjustment of the ionic strength between conductivities of 8 mS/cm to 22.5 mS/cm may be required to enable selective precipitation. Preferably, for the separation of Fab from the Fc region the ionic strength is adjusted to conductivities between 9 mS/cm and 18 mS/cm, most preferred between 10 and 16 mS/cm.

The pH is preferably adjusted using appropriate methods to achieve a pH lower than the isoelectric point (pI) of the target molecule and, if applicable to a pH above the isoelectric point of the impurity proteins or most of the impurity proteins. It has been found that typically the pH should be adjusted to 4 to 7, preferably to 4 to 5.5. Especially when precipitating monoclonal antibodies with isoelectric point between 7 and 9 from cell culture fluids like NS0, CHO-S or SP2/0 cell culture fluids, a pH between 4 and 5.5, especially a pH between 5.0 and 5.2 is very suitable.

In specific cases, notably separation of Fab from the Fc region after enzymatic treatment of a monoclonal antibody, adjustment of the pH to a pH between 4 and 5.5, especially a pH between 5.0 and 5.2 is very suitable.

The amount of copolymer to be used for the method of the present invention is dependent from the amount of target molecule that is present in the sample. Typically, good results can be obtained when using between 0.2 and 1.2 mg copolymer per mg target molecule. Preferably, between 0.35 and 0.9 mg copolymer are added per mg target molecule.

To achieve optimal precipitation, after adding the copolymer to the sample solution, the mixture is preferably incubated. Typical incubation times are between 10 minutes and 2 hours. Preferably the mixture is agitated during incubation, e.g. on a shaker or with a stirrer.

Afterwards, the co-precipitate comprising the target molecule and the copolymer can be isolated from the supernatant, e.g. by filtration, sedimentation, centrifugation or any other means. Typically, the co-precipitate comprising the target molecule is then subjected to further process steps for isolating or further purifying the target molecule. But it is also possible to subject the supernatant to further process steps. E.g. in case the target molecule is a known substance that shall be removed from the sample (e.g. Fc region of an antibody) but the product to be finally isolated and purified from the sample is another molecule that after performing the process of the present invention is now present in the supernatant (e.g. Fab region of an antibody).

But in most cases, the target molecule that has been precipitated by adding the copolymer is the compound that shall be further purified. In this case, the co-precipitate comprising the target molecule may be washed one or several times e.g. with an acidic buffer. Preferably the wash buffer has the same pH and same or lower ionic strength as the mixture obtained after adding the copolymer to the sample.

The co-precipitate may then be re-dissolved. This can be done in an aqueous buffer having a pH above one pH-unit below the isoelectric point of the target molecule. Typically a buffer with a pH between 7 and 9 is used for re-dissolving the co-precipitate, e.g. Tris-buffer pH 8.0 or K—Na-Phosphate Buffer pH 7.4 (PBS). The re-dissolving can be supported e.g. by shaking or stirring, e.g. shaking for 5 to 20 minutes at 300 to 600 rpm.

In one embodiment of the present invention, to obtain a highly purified target molecule, in a further step of the method according to the present invention the copolymer can be removed from the solution comprising the re-dissolved co-precipitate. This can be done by several methods like chromatographic methods, e.g. anion exchange chromatography, cation exchange chromatography, hydrophobic interaction chromatography, hydrophilic interaction chromatography or affinity chromatography. It is also possible to re-precipitate the copolymer by adding a precipitant. Suitable precipitants are for example beads to which polyelectrolytes are covalently attached. Polyelectrolytes are polymers whose repeating units bear an electrolyte group. Polycations and polyanions are polyelectrolytes.

Examples of suitable beads are e.g. glass beads, silica beads or polymer beads. Suitable polyelectrolytes are for example cationic polyelectrolytes, mixed mode polyelectrolytes, hydrophobic polyelectrolytes or hydrophilic polyelectrolytes able to do H-bonding.

Suitable beads are e.g. disclosed in U.S. Pat. No. 5,922,531.

In a preferred embodiment, the beads are glass or silica beads, more preferably glass or mica or silica flakes. It has been found that glass or silica flakes with a sedimentation speed between 0.8 and 1.2 cm/min are especially suitable for the re-precipitation. Typically, silica or glass flakes with a diameter ranging from 10-200 μM and a thickness between 100 and 1000 nm show such suitable sedimentation speed and are especially suitable for re-precipitating the copolymers. In a preferred embodiment, the glass or silica beads and also other types of beads are functionalized with cationic groups or cationic and hydrophobic or hydrophilic groups.

Preferably the functionalization is made by covalent bonding of cationic polyelectrolytes or polyelectrolytes with cationic and hydrophobic or hydrophilic functionalities.

Especially preferred are polyelectrolytes comprising TMAE or DMAE.

The beads are typically added to the resuspended target-molecule-copolymer solution to reach a final concentration of the beads or flakes in the final mixture of between 0.0001 and 0.5 mg/ml.

The beads are typically added to the resuspended target-molecule-copolymer solution after adjusting the pH of the solution to pH 7.0-8.5.

After removing the beads with the attached copolymer, e.g. by centrifuging, sedimentation or filtering, one obtains the supernatant comprising highly pure target molecule and no or little copolymer contamination. Typically, copolymer can be removed to >90% (weight/weight) compared to the initial copolymer concentration within a sample, using these silica flakes.

Adjusting the concentration of these silica flakes, copolymer can be removed to typically >95% (weight/weight) up to 99% (weight/weight) compared to the initial copolymer concentration within a sample.

The method of the invention reduces impurities and prevents clogging of subsequent purification steps like chromatography, filtration or centrifugation. The method of the present invention can up-concentrate the target molecule by selective precipitation and subsequent redissolution in a defined volume, achieving concentration factors of up to 100, thereby increasing processing time for subsequent purification steps and reducing the workload for chromatography (hours/kg target molecule purified in chromatography).

While the use of polymers for precipitation disclosed in prior art often gives high purification yields, it only works sufficiently at ionic strength as low as a conductivity of 5 mS/cm or less as shown in these publications.

However, this restriction requires dilution of cell culture fluid prior application of polymers for precipitation, e.g. mounting to 75000 liters diluted cell culture fluid and more, compared to 25000 liters of initial cell culture fluid.

These large volumes need to be tempered, stored and have a high waste load after purification, all leading to high costs.

In contrast to these restrictions and disadvantages, the method of the present invention enables customers to use specifically optimized copolymers in order to obtain a high yield and purity of target molecule, even at ionic strength similar to physiological salt conditions. Thereby excessive pre-dilution steps are not required.

The invention can replace partially or fully, to date used purification steps in the purification of a biopharmaceutical or recombinant protein, leading to equal or better yield, purification time, efficiency, purity.

The entire disclosures of all applications, patents, and publications cited above and below and of corresponding EP application EP 12008475.1, filed Dec. 20, 2012, are hereby incorporated by reference.

EXAMPLES

The following examples represent possible synthesis steps to obtain copolymers used in the method of the invention Example 1a 4.92 g of 2-acrylamido-2-methylpropane sulfonic acid and 6.82 g of 4-acrylamido benzoic acid are dissolved in a mixture of 300 ml water/DMF (1/1) and 3.4 ml NaOH solution (32%). The solution is degassed using nitrogen. 0.436 g of sodiumperoxodisulfate dissolved in degassed water are added to the solution. The temperature is raised to 80° C. Reaction time is 5 hours. The reaction mixture is cooled to room temperature and exposed to air. The solvent is removed with a rotary evaporator. The solid polymer is dissolved again in water and precipitated in 2-propanol. The polymer is filtered and dried. The weight average molecular weight is approximately Mw=100 000 g/mol, with a polydispersity of 1.3.

Example 1b

Same as example 1a, but purification of polymer using a Sephadex® column (crosslinked dextrane gel). The column is washed with 5×5 ml water, 2.5 ml of the reaction mixture are "injected" and the column washed with 3.5 ml water. The eluate is collected and re-equilibration done with 7×5 ml water. The procedure is repeated 3 times. The solvent is removed from the eluate using a rotary evaporator and the polymer is dried.

Example 1c

Same as example 1a, but purification through dialysis or tangential flow filtration. After the reaction, the mixture is cooled to room temperature and the solvent is removed with a rotary evaporator. The solid polymer is dissolved again in water and the polymer purified with dialysis using an appropriate MWCO of e.g. 12 000-14 000 Da or tangential flow filtration.

Example 2a 4.92 g of 2-acrylamido-2-methylpropane sulfonic acid and 6.82 g of 4-acrylamido benzoic acid are dissolved in a mixture of 300 ml water/DMF (1/1) and 3.4 ml NaOH solution (32%). 95 µL 1-butanethiol (as chain transfer agent) are added. The solution is degassed using nitrogen. 0.436 g of sodiumperoxodisulfate dissolved in degassed water are added to the solution. The temperature is raised to 80° C. Reaction time is 5 hours. The reaction mixture is cooled to room temperature and exposed to air. The solvent is removed with a rotary evaporator. The solid polymer is dissolved again in water and precipitated in 2-propanol. The polymer is filtered and dried. The weight average molecular weight is approximately Mw=55 000 g/mol, with a polydispersity of 1.16.

Example 2b

Same as example 2a, but 380µl of 1-butanethiol are added. The weight average molecular weight of the resulting polymer is approximately Mw=35 000 g/mol, with a polydispersity of 1.6.

Example 3

Same as example 1, but different molar monomer ratios are used:

| example | 2-acrylamido-2-methylpropane sulfonic acid | 4-acrylamido benzoic acid |
|---------|--------------------------------------------|---------------------------|
| 3a      | 1                                          | 0                         |
| 3b      | 1                                          | 0.3                       |

-continued

| example | 2-acrylamido-2-methylpropane sulfonic acid | 4-acrylamido benzoic acid |
|---|---|---|
| 3c | 1 | 0.7 |
| 3d | 1 | 1.5 |
| 3e | 1 | 3 |
| 3f | 0 | 1 |

Example 4

Same as example 3 but instead of 4-acrylamido benzoic acid, benzylacrylamide is used as co-monomer.

The following examples show applications of the invention

Example 5

A monoclonal antibody cell culture solution (SP2/0 cell culture fluid) with a monoclonal antibody (mAb03) titer of 2.0 mg/ml (according to Protein A affinity chromatography), where HCP (host cell protein) amount is 9000 ng/mg antibody (according to immunoenzymetric-assay SP2/0) is treated with anionic-hydrophobic copolymers after prior adjustment of the cell culture solution to pH 5.0. The copolymer is synthesized with 61.7% (w/w) AMPS and 38.3% (w/w) (ABZ), using 3.17% (w/w) Sodiumperoxodisulphate and chain transfer agent 1-Butanthiol at a ratio of 1:0.03 of overall monomer concentration (AMPS+ABZ) in mol.

Characterization of the copolymer yields (36% 4-(Acryloylamino)benzoic acid (ABZ FIG. 1) (w/w); 64% 2-Acrylamido-2-methylpropane sulfonic acid (AMPS FIG. 1) (w/w); determined by Attenuated total reflection infrared spectroscopy; molecular weight distribution determined by differential refractive index on SEC: Mw 28000 Da, Mn 13000 Da, polydispersity index 2.1. Copolymer is adjusted to a concentration of 10 mg/ml pH 5.0 and added in small volume to the antibody cell culture solution to final concentrations ranging from 0.4 mg/ml polymer to 1.2 mg/ml polymer and final antibody concentrations of 1.4 mg/ml (ionic strength: conductivity of 12 mS/cm or 120 mM NaCl equivalents, measured at 20° C.).

Figure 2:
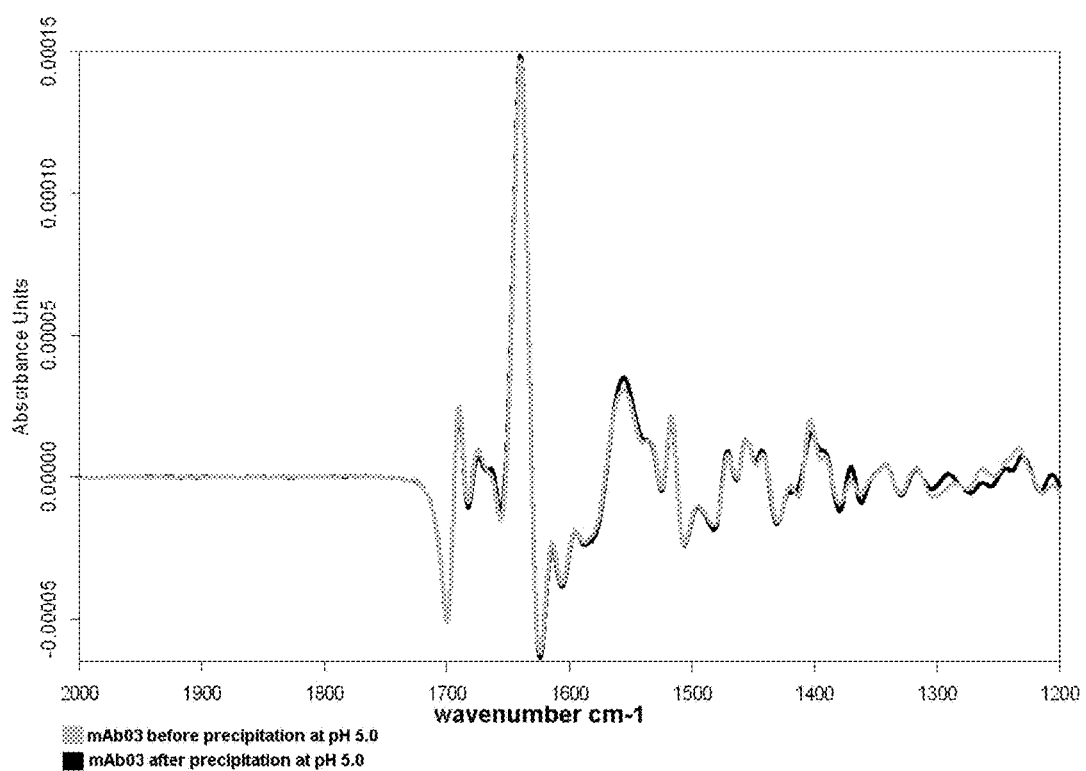
FIG. 2 shows mid infrared spectra as spectral overlay to compare
a) monoclonal antibody Cetuximab which has been treated with the purification techniques according to the present invention
b) secondary structure of monoclonal antibody Cetuximab not subjected to precipitation
and show that the secondary structure of the antibody is not significantly altered upon precipitation.

After one hour slow stirring, antibody cell culture with added copolymer is centrifuged for 15 minutes at 2500 rcf. Supernatant is discarded and pellet redissolved in 80 mM K—Na-Phosphate buffer pH 7.4 by shaking for 12 minutes at 500 rpm. Quarternary ammonia residue (Trimethylaminoethyl) attached to silica flakes are added to the redissolved pellet at a ratio of 10% (v/v), followed by 10 minutes centrifugation at 2500 rcf. Supernatant is removed and yields copolymer removal of 98.8%, HCP removal of 70% and antibody recovery of 80% compared to initial antibody titer. IR spectra (see attached FIG. 2) show no significant changes of the secondary structure of the antibody before and after precipitation, followed by redissolution. Biolayer Interferometry (BLI) shows no difference in binding affinity of the antibody to its target, comparing non-precipitated antibody (see attached FIG. 3 A) with antibody purified using precipitation and redissolution according to this invention (see attached FIG. 3 B).

Example 6

A solution which contains 2 mg/ml monoclonal antibody (mAb03, mAb04, mAb05, mAb07, respectively, additional information table 2) and 2 mg/ml bovine serum albumin is treated with various anionic-hydrophobic copolymers after prior adjustment of the cell culture solution to pH 5.0. The copolymers (10-77.5% ABZ (w/w); 22.5-90% AMPS (w/w); determined by Attenuated total reflection spectroscopy; molecular weight distribution determined by refractive index on SEC: Mw 5000-300000 Da, Mn 5000-131000 Da, polydispersity index 1—2.3; molecular weight distribution determined by UV measurement on SEC: Mw 5000-300000 Da, Mn 5000-131000 Da, polydispersity index 1—2.5) are added to the solutions (each copolymer at each concentration, each pH and ionic strength is added to a separate solution container) to constitute a copolymer-protein solution with final antibody concentration of 1 mg/ml final BSA concentration of 1 mg/ml, pH 5.0, ionic strength approximately conductivity of 15 mS/cm, measured at 20° C. and copolymer concentration of 0.1-1.5 mg/ml. After one hour shaking at 300 rpm, copolymer-protein solution is centrifuged for 15 minutes at 2500 rcf. Supernatant is discarded and pellet redissolved in 80 mM K—Na-Phosphate buffer pH 7.4 by shaking for 12 minutes at 500 rpm. 10% (v/v) TMAE flakes are added to the redissolved pellet, followed by 10 minutes centrifugation at 2500 rcf. Supernatant is removed and yields copolymer removal of 95%, BSA removal of 20-80% and antibody recovery of 85% compared to initial antibody titer. Most promising copolymers (10-70% ABZ, 30-90% AMPS, weight average chain length <80000Da) yield 85% mAb recovery and 80% BSA removal.

TABLE 2 target proteins used in precipitation experiments

| protein | Lysozyme | BSA | mAb03 | mAb04 | mAb05 | mAb07 | Fab |
|---|---|---|---|---|---|---|---|
| isoelectric point | 10.7 | 4.9 | 8-9 | 8-9 | 8-9 | 7-8 | 8-9 |
| molecular weight in kDa | 14.3 | 66 | 150 | 150 | 150 | 150 | ~50 |
| hydropathicity index: Gravy | −0.472 | −0.429 | −0.413 | −0.42 | −0.343 | −0.459 | −0.310 |

Example 7

A monoclonal antibody cell culture solution in CHO-S cell line which contains 0.7 mg/ml monoclonal antibody (mAb05) and a known amount of HCP proteins/mg antibody is adjusted to pH 5.0 and a conductivity of 11 mS/cm, measured at 20° C. The solution is treated with an anionic-hydrophobic copolymer (65% ABZ, 35% AMPS; Mw 80000 Da, Mn 55000 Da, determined by differential refractive index on SEC) at final copolymer to antibody weight ratios of 0.57:1 to 1.14:1. After shaking for one hour at 300 rpm and centrifugation at 2500 rcf for 15 minutes, the supernatant is transferred and analyzed as well as the redissolved pellet (80 mM K—Na-Phosphate buffer pH 7.4 by shaking for 12 minutes at 500 rpm). Both determinations show a host cell protein removal of 50% and antibody precipitation of 80-90%. Middle infrared spectra reveal no structural changes of the antibody before and after precipitation consistent with literature searches. Biolayer interferometry shows no change in the binding affinity of the antibody before and after precipitation.

Example 8

A solution containing the FAb part (fragment antigen-binding) of a monoclonal antibody (mAb03) at a concentration of 2 mg/ml is adjusted to pH 5.0 with an ionic strength of a conductivity of 2 mS/cm (measured at 20° C.) before adding 100% (v/v) of an anionic-hydrophobic copolymer (50% BzAAm, 50% AMPS; Mw 63000, Mn 46000, determined by refractive index measurement on SEC) to a final concentration of 0.1-0.8 mg/ml in the FAb-copolymer solution (ionic strength with conductivity of 1 mS/cm, pH 5.0). Solution is incubated on shaker for one hour at 300 rpm and centrifuged for 15 minutes at 2500 rcf. 80% FAb are precipitated from the solution.

Example 9

A monoclonal antibody cell culture solution in murine myeloma cell line (NS0) which contains 2 mg/ml monoclonal antibody (mAb07) and a known amount of HCP proteins/mg antibody is adjusted to pH 5.0 conductivity of 12 mS/cm and treated with an anionic-hydrophobic copolymer (65% ABZ, 35% AMPS; Mw 80000 Da, Mn 55000 Da, determined by refractive index on SEC) at various final copolymer to antibody weight ratios. After shaking for one hour at 300 rpm and centrifugation at 2500 rcf for 15 minutes, the supernatant is transferred and analyzed as well as the redissolved pellet (80 mM K—Na-Phosphate buffer pH 7.4 by shaking for 12 minutes at 500 rpm). Both determinations show a host cell protein removal of 50-70% and antibody precipitation of 80-95%.

Example 10 same as Example 9, but initial volume of precipitation is 20 mL and target-molecule-copolymer pellet is redissolved in 500 uL, increasing the target-molecule concentration by factor 40.

Example 11

A solution containing Fab and Fc fragments of a monoclonal antibody after papain digestion was adjusted to pH 5.0 and a conductivity of 14 mS/cm. The solution was treated with an anionic-hydrophobic copolymer (64% ABZ, 36% AMPS; Mw 160,000 Da, Mn 55000 Da, determined by refractive index on SEC) at various final copolymer to overall protein weight ratios. After shaking for one hour at 300 rpm and centrifugation at 2500 rcf for 15 minutes, the supernatant is transferred and analyzed as well as the redissolved pellet (80 mM K—Na-Phosphate buffer pH 7.4 by shaking for 12 minutes at 500 rpm). The pellet consisted of only Fc fragment, while the supernatant was composed of 10% non-precipitated Fc and 100% of initially employed Fab fragment.

Example 12

Silica or Diol Glass Flake—TMAE Synthesis

Silica or diol glass flakes are synthesized using Diol glass flakes or silica flakes coated with glycidyloxipropyltriethoxysilan with 10-100 μm diameter and adding monomers N,N-Dimethylethylendiamine (0.225 M), Acrylic acid chloride (0.216 M) and Dimethylsulphate (0.228 M), using 4.5 mM Ammoniumcer-IV-nitrat as initiator.

Other Issues

The copolymer compositions are characterized using NMR spectroscopy as well as attenuated total reflection spectroscopy (ATR) with infrared spectroscopy. Results are comparable between NMR and ATR (table 3), showing the feasibility of ATR for copolymer characterization.

TABLE 3

Comparison ATR-IR vs NMR for copolymer analysis

| | NMR | | | ATR | | | Ratio during synthesis | | |
|---|---|---|---|---|---|---|---|---|---|
| Co-polymer | % (w/w) AMPS | % (w/w) BzAAm | % (w/w) ABZ | % (w/w) AMPS | % (w/w) BzAAm | % (w/w) ABZ | % (w/w) AMPS | % (w/w) BzAAm | % (w/w) ABZ |
| pol35 | 19 | | 81 | 20 | | 81 | 27 | | 73 |
| pol30 | 36 | | 64 | 37 | | 63 | 42 | | 58 |
| pol12 | 43 | 57 | | 48 | 52 | | 63 | 47 | |
| pol8 | 54 | 46 | | 54 | 46 | | 49 | 51 | |

Table 4 shows examples of copolymers to be used according to the method of the present invention that have been prepared according to the procedures described in Examples 1-4.

TABLE 4

| Co-polymer | % (w/w) AMPS by ATR | % (w/w) ABZ by ATR | % (w/w) BzAAm by ATR | Mw (g mol$^{-1}$ by refractive index of SEC) |
|---|---|---|---|---|
| pol1 | 95 | 0 | 5 | 56000 |
| pol2 | 93 | 0 | 7 | 28244 |
| pol3 | 82 | 0 | 18 | 78000 |
| pol4 | 81 | 0 | 19 | 46014 |
| pol5 | 81 | 0 | 19 | 112873 |
| pol7 | 54 | 0 | 46 | 11757 |
| pol8 | 54 | 0 | 46 | 44000 |
| pol10 | 49 | 0 | 51 | 63000 |
| pol12 | 36 | 0 | 64 | 9136 |
| pol15 | 38 | 0 | 62 | 63000 |
| pol16 | 83 | 17 | 0 | 82000 |
| pol18 | 61 | 39 | 0 | 114000 |
| pol19 | 65 | 35 | 0 | 38800 |
| pol20 | 59 | 41 | 0 | 66690 |
| pol21 | 59 | 41 | 0 | 34600 |
| pol22 | 49 | 51 | 0 | 58700 |

TABLE 4-continued

| Co-polymer | % (w/w) AMPS by ATR | % (w/w) ABZ by ATR | % (w/w) BzAAm by ATR | Mw (g mol$^{-1}$ by refractive index of SEC) |
|---|---|---|---|---|
| pol23 | 44 | 56 | 0 | 81000 |
| pol24 | 43 | 57 | 0 | 95000 |
| pol26 | 39 | 61 | 0 | 124000 |
| pol30 | 37 | 63 | 0 | 43000 |
| pol33 | 27 | 73 | 0 | 75000 |
| pol35 | 20 | 80 | 0 | 108000 |

Table 5 shows the ionic strength of protein expression systems used in precipitation experiments

TABLE 5

| protein expression system | E. coli | chinese hamster ovary cells (CHO) | CHO-DG44 | murine myeloma (NS0) | SP2/0 |
|---|---|---|---|---|---|
| ionic strength (conductivity measured at 20° C.) | 10-15 mS/cm | ~11-17 mS/cm | ~11-17 mS/cm | ~11-17 mS/cm | ~11-17 mS/cm |

The invention claimed is:

1. A method for isolating a target molecule from a sample comprising:
   a) adjusting the pH of the sample to a pH below the isoelectric point of the target molecule,
   b) mixing one or more copolymers with the sample, wherein the copolymer is synthesized from monomer units whereby each monomer unit that is used for synthesizing the copolymer has at least one hydrophobic or one anionic group, wherein the copolymer is obtained from
      (i) monomers of 2-acrylamido-2-methylpropane sulfonic acid and 4-acrylamido benzoic acid, or
      (ii) monomers of 2-acrylamido-2-methylpropane sulfonic acid and benzylacrylamide, whereby a target molecule-copolymer precipitate is formed, and
   c) separating the precipitate from the mixture of b), wherein the target molecule is an antibody, an Fc fragment of an antibody, or an Fab fragment of an antibody.

2. The method according to claim 1, wherein 35 to 65% of the hydrophobic and anionic groups of the copolymer are anionic groups.

3. The method according to claim 1, wherein the copolymer has a weight average molecular weight between 10,000 and 120,000 g/mol and/or a polydispersity between 1.05-2.5.

4. The method according to claim 1, wherein the target molecule is an antibody.

5. The method according to claim 1, wherein in a) the pH of the sample is adjusted to a pH between 4 and 5.5.

6. The method according to claim 1, wherein the ionic strength of the sample is adjusted to be equal to a conductivity of 17 mS/cm or less, measured at 20° C.

7. The method according to claim 1, wherein the target molecule is a fragment antigen binding region.

8. The method according to claim 7, the ionic strength of the sample is adjusted to be equal to a conductivity of between 9 and 18 mS/cm, measured at 20° C.

9. The method according to claim 1, further comprising d) re-dissolving the precipitate from c).

10. The method according to claim 9, wherein the re-dissolved mixture of d) is treated with beads carrying polyelectrolytes.

11. The method according to claim 10, wherein the beads carrying polyelectrolytes are glass or silica flakes.

12. The method according to claim 11, wherein the polyelectrolytes comprise DMAE and/or TMAE groups.

13. The method according to claim 4, wherein said antibody is an Fc region containing protein, and said Fc region containing protein is a recombinant protein which includes the Fc region of an immunoglobulin fused to another polypeptide or a fragment thereof.

14. The method according to claim 1, wherein said sample is obtained from a mammalian cell culture, a bacterial cell culture, a yeast cell culture, or filamentous fungi.

15. The method according to claim 2, wherein 45 to 60% of the hydrophobic and anionic groups of the copolymer are anionic groups.

16. The method according to claim 1, wherein the ionic strength of the sample mixed with the one or more copolymers in b) is 10 mS/cm to 22.5 mS/cm, determined at 20° C.

* * * * *